United States Patent
Dallaire et al.

(10) Patent No.: US 11,274,338 B2
(45) Date of Patent: Mar. 15, 2022

(54) METHODS FOR SEQUENTIALLY PREPARING DIFFERENT TEST SAMPLES FROM A SINGLE DRIED BLOOD SAMPLE

(71) Applicant: PerkinElmer Health Sciences, Inc., Waltham, MA (US)

(72) Inventors: Stephanie Dallaire, Waltham, MA (US); Jordan Haddock, Waltham, MA (US); Cristina Gutierrez-Mateo, Waltham, MA (US); Anna M. Potier, Waltham, MA (US); Joseph D. Trometer, Waltham, MA (US)

(73) Assignee: PerkinElmer Health Sciences, Inc., Waltham, MA (US)

(*) Notice: Subject to any disclaimer, the term of this patent is extended or adjusted under 35 U.S.C. 154(b) by 297 days.

(21) Appl. No.: 16/473,062

(22) PCT Filed: Oct. 15, 2018

(86) PCT No.: PCT/US2018/055872
§ 371 (c)(1),
(2) Date: Jun. 24, 2019

(87) PCT Pub. No.: WO2019/075460
PCT Pub. Date: Apr. 18, 2019

(65) Prior Publication Data
US 2020/0283835 A1 Sep. 10, 2020

Related U.S. Application Data

(60) Provisional application No. 62/571,945, filed on Oct. 13, 2017.

(51) Int. Cl.
*C12Q 1/6806* (2018.01)
*C12Q 1/6851* (2018.01)
*C12Q 1/24* (2006.01)
*G01N 33/68* (2006.01)

(52) U.S. Cl.
CPC ............ *C12Q 1/6851* (2013.01); *C12Q 1/24* (2013.01); *C12Q 1/6806* (2013.01); *G01N 33/6848* (2013.01)

(58) Field of Classification Search
CPC ...... C12Q 1/6806; C12Q 1/6851; C12Q 1/24; G01N 33/6848
See application file for complete search history.

(56) References Cited

U.S. PATENT DOCUMENTS

| 2012/0273671 A1 | 11/2012 | La Marca et al. |
| 2015/0040688 A1* | 2/2015 | Murphy ................. B23K 26/16 73/863 |
| 2016/0061836 A1 | 3/2016 | Potier |

FOREIGN PATENT DOCUMENTS

WO 2017070643 A1 4/2017

OTHER PUBLICATIONS

Zhang, X. K. et al., 'Multiplex lysosomal enzyme activity assay on dried blood spots using tandem mass spectrometry', Methods in Molecular Biology, 2010, vol. 603, p. 339-350.
Ali, N. et al., 'Current nucleic acid extraction methods and their implications to point-of-care diagnostics', BioMed Research International, Jul. 12, 2017, vol. 2017, Article ID 9306564, pp. 1-13.

* cited by examiner

*Primary Examiner* — David C Thomas
(74) *Attorney, Agent, or Firm* — Dinsmore & Shohl LLP; Weston R. Gould

(57) ABSTRACT

Provided are processes for the use of a single dried blood sample for the preparation of test samples including targets of differing structures. The processes allow the same dried blood sample to be used for preparation of a first test sample including a non-nucleic acid target, and the same dried blood sample to be subsequently processed for preparation of a test sample that includes a nucleic acid target whereby the processes preserve the ability of the nucleic acid to be detected in subsequent detection assays following prior isolation of non-nucleic acid targets.

20 Claims, 4 Drawing Sheets

Specification includes a Sequence Listing.

SEQUENCE LISTING

<160> NUMBER OF SEQ ID NOS: 13

<210> SEQ ID NO 1
<211> LENGTH: 21
<212> TYPE: DNA
<213> ORGANISM: Artificial Sequence
<220> FEATURE:
<223> OTHER INFORMATION: TREC Forward Primer

<400> SEQUENCE: 1
tttgtaaagg tgcccactcc t                                           21

<210> SEQ ID NO 2
<211> LENGTH: 26
<212> TYPE: DNA
<213> ORGANISM: Artificial Sequence
<220> FEATURE:
<223> OTHER INFORMATION: TREC Reverse Primer

<400> SEQUENCE: 2
tattgcaact cgtgagaacg gtgaat                                    26

<210> SEQ ID NO 3
<211> LENGTH: 19
<212> TYPE: DNA
<213> ORGANISM: Artificial Sequence
<220> FEATURE:
<223> OTHER INFORMATION: TREC Probe

<400> SEQUENCE: 3
cggtgatgca taggcacct                                            19

<210> SEQ ID NO 4
<211> LENGTH: 27
<212> TYPE: DNA
<213> ORGANISM: Artificial Sequence
<220> FEATURE:
<223> OTHER INFORMATION: KREC Forward Primer

<400> SEQUENCE: 4
tcccttagtg gcattatttg tatcact                                   27

<210> SEQ ID NO 5
<211> LENGTH: 24
<212> TYPE: DNA
<213> ORGANISM: Artificial Sequence
<220> FEATURE:
<223> OTHER INFORMATION: KREC Reverse Primer

<400> SEQUENCE: 5
aggagccagc tcttaccta gagt                                       24

<210> SEQ ID NO 6
<211> LENGTH: 21
<212> TYPE: DNA
<213> ORGANISM: Artificial Sequence
<220> FEATURE:
<223> OTHER INFORMATION: KREC Probe

<400> SEQUENCE: 6
tctgcacggg cagcaggttg g                                         21

<210> SEQ ID NO 7
<211> LENGTH: 31
<212> TYPE: DNA
<213> ORGANISM: Artificial Sequence
<220> FEATURE:
<223> OTHER INFORMATION: SMN Forward Primer

<400> SEQUENCE: 7
cttgtgaaac aaaatgcttt ttaacatcca t                              31

<210> SEQ ID NO 8
<211> LENGTH: 25
<212> TYPE: DNA
<213> ORGANISM: Artificial Sequence
<220> FEATURE:
<223> OTHER INFORMATION: SMN Reverse Primer

<400> SEQUENCE: 8
gaatgtgagc accttccttc ttttt                                     25

<210> SEQ ID NO 9
<211> LENGTH: 17
<212> TYPE: DNA
<213> ORGANISM: Artificial Sequence

```
<220> FEATURE:
<223> OTHER INFORMATION: SMN Probe
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 9
aggngttntn cnangac                                                   17

<210> SEQ ID NO 10
<211> LENGTH: 18
<212> TYPE: DNA
<213> ORGANISM: Artificial Sequence
<220> FEATURE:
<223> OTHER INFORMATION: SMN Probe
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 10
agngngttnt ntnangac                                                  18

<210> SEQ ID NO 11
<211> LENGTH: 16
<212> TYPE: DNA
<213> ORGANISM: Artificial Sequence
<220> FEATURE:
<223> OTHER INFORMATION: RPP30 Forward Primer

<400> SEQUENCE: 11
tttggacctg cgagcg                                                    16

<210> SEQ ID NO 12
<211> LENGTH: 20
<212> TYPE: DNA
```

```
<213> ORGANISM: Artificial Sequence
<220> FEATURE:
<223> OTHER INFORMATION: RPP30 Reverse Primer

<400> SEQUENCE: 12
gagcggctgt ctccacaagt                                              20

<210> SEQ ID NO 13
<211> LENGTH: 23
<212> TYPE: DNA
<213> ORGANISM: Artificial Sequence
<220> FEATURE:
<223> OTHER INFORMATION: RPP30 Probe

<400> SEQUENCE: 13
ttctgacctg aaggctctgc gcg                                          23
```

METHODS FOR SEQUENTIALLY PREPARING DIFFERENT TEST SAMPLES FROM A SINGLE DRIED BLOOD SAMPLE

CROSS REFERENCE TO RELATED APPLICATIONS

This application is a U.S. National Stage of PCT/US2018/055872 filed Oct. 15, 2018, which depends from and claims priority to U.S. Provisional Application No. 62/571,945 filed Oct. 13, 2017, the entire contents of which are incorporated herein by reference.

SEQUENCE LISTING

This application incorporate by reference a Sequence Listing as an ASCII text file entitled "16NEN26102PA_ST25_corrected2" created on Mar. 26, 2020 having a size of 3595 bytes.

BACKGROUND

Myriad medical tests are performed using blood samples. One method for preparing blood samples is to absorb blood droplets on a paper filter. Blood preserved in this manner can be stored and shipped at ambient temperature and is a favored method for collecting and storing newborn infant blood samples in the United States. Samples so prepared are known as "dried blood spots" (DBS).

Medical tests are performed on DBS by punching a fractional portion of the blood-absorbed filter paper into a receptacle, which is typically a well of a multi-well sample plate. The punched portion is then soaked in a solution to release some of the blood material. This released material becomes a test sample, and the test sample is analyzed to assess a health condition.

However, when multiple tests are desired it is common practice to require different collection methods and additional collection samples to allow for the use of multiple testing protocols. This increases both the expense and time required to derive a result from multiple samples as well as necessitating additional sample collection either at the same time or a second time from a subject. In many instances, a sample is taken from a baby born pre-maturely or a baby that produces miniscule amounts of blood and the DBS is either too small or contains too little DNA to obtain more than one sample from the DBS. In these instances, it would be advantageous to use a single sample to obtain multiple diagnostic results.

As such, there is a need for new and efficient methods of analyzing biomarkers and other sample components from dried blood spots.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

Provided are methods of analyzing multiple types of analytes from a single sample thereby improving throughput and reducing measurement errors. A method as provided includes obtaining a dried blood sample, contacting the dried blood sample with an elution solution optionally comprising a C1-3 linear or branched chain monoalcohol, incubating the dried blood sample in the elution solution for a time sufficient to elute one or more non-nucleotide targets, separating the dried blood sample and the elution solution, thereby preparing a first test sample comprising the non-nucleotide targets and a separated dried blood sample, contacting the separated dried blood sample with nucleic acid releasing solution suitable for eluting nucleic acids, and incubating the separated dried blood sample in the nucleic acid releasing solution for a time sufficient to elute the nucleic acids, thereby preparing a second test sample.

Other methods are provided that utilize an elution solution that is capable of sustaining enzymatic activity of one or more target proteins such that the enzymatic activity of the target proteins may be analyzed. Such processes include obtaining a dried blood sample, contacting the dried blood sample with an elution solution capable of sustaining enzymatic activity of one or more target proteins, incubating the dried blood sample in the elution solution for a time sufficient to elute the one or more target proteins, subsequently contacting the post-incubation dried blood sample with a quenching agent to produce a quench solution that inhibits enzymatic activity of the one or more target proteins, separating the dried blood sample and the quench solution, thereby preparing a first test sample comprising the one or more target proteins and a separated dried blood sample, contacting the separated dried blood sample with nucleic acid releasing solution suitable for eluting nucleic acids, and incubating the separated dried blood sample in the nucleic acid releasing solution for a time sufficient to elute the nucleic acids, thereby preparing a second test sample.

Optionally for either method a protein or metabolite sample may be analyzed by mass spectrometry. Optionally for either method a nucleic acid may be analyzed by polymerase chain reaction, optionally quantitative PCR.

BRIEF DESCRIPTION OF THE DRAWINGS

The aspects set forth in the drawings are illustrative and exemplary in nature and not intended to limit the subject matter defined by the claims. The following detailed description of the illustrative aspects can be understood when read in conjunction with the following drawings, and in which:

DESCRIPTION

Figure 1:
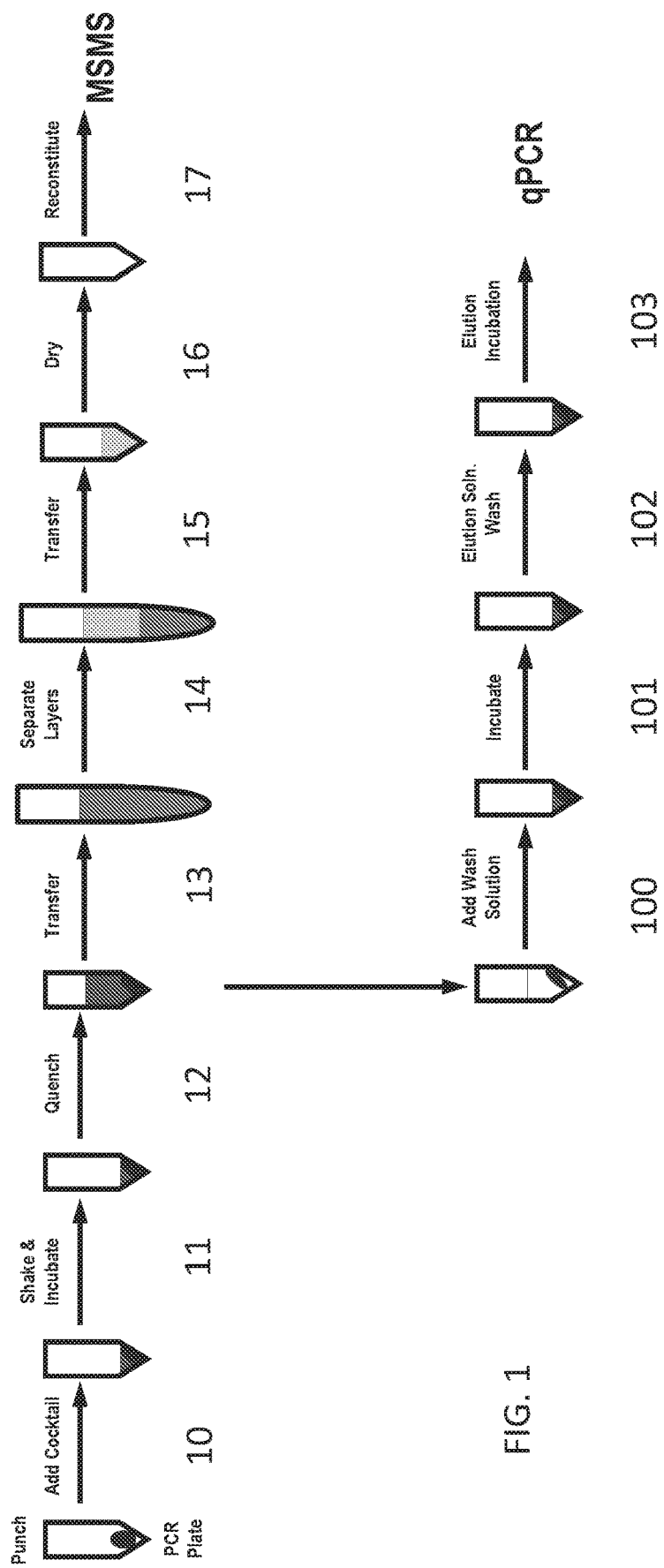
FIG. 1 illustrates an exemplary method of detecting the presence or absence of enzymes related to a series of lysosomal storage disorders and nucleic acids from both genomic and non-genomic sources using an alkaline based nucleotide extraction method from the same dried blood spot sample according to some aspects as provided herein.

The following description is merely exemplary in nature and is in no way intended to limit the scope of the invention, its application, or uses, which may, of course, vary. The disclosure is presented in relation to the non-limiting definitions and terminology included herein. These definitions and terminology are not designed to function as a limitation on the scope or practice of the disclosure but are presented for illustrative and descriptive purposes only. While the processes or compositions are described as an order of individual steps or using specific materials, it is appreciated that steps or materials may be interchangeable such that the description may include multiple parts or steps arranged in many ways as is readily appreciated by one of skill in the art.

It will be understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Samples in the form of a dried blood sample (DBS) are commonly used when screening blood from newborns and child patients. To prepare these samples, blood is typically collected from the subject such as by a finger, toe, or foot prick and retained on filter paper. The use of a single dry blood sample for the elution of multiple target types of differing chemical composition are provided herein. The processes as described are capable of detecting both enzymes/protein/metabolites from a dried blood sample and using the same dried blood sample for the detection of nucleic acids of genomic and non-genomic origin. The provided processes avoid the need to obtain several punches (or other segments) from the same sample, or to collect aliquots of other sample sources, and accordingly reduces variation caused by inhomogeneous distribution of blood on the filter paper and errors in sample transfer.

According to some aspects of a process as provided herein a blood material is released from the DBS using a solution suitable for isolating target material of non-nucleic acid form. This first solution of material of a non-nucleic acid form is termed a first test sample that is amenable to subsequent processing and/or analyses for detection or quantification of the non-nucleic acid target material. Second, the same DBS sample is transferred to a new receptacle and used to isolate nucleic acid materials of a genomic or non-genomic state. The resulting solution of nucleic acid is termed a second test solution as used herein. This second test solution may be effectively subjected to further analyses for detection and or quantification of nucleic acid within the second test sample.

The processes provided herein involve sequentially preparing different test samples from a single dried blood sample. For example, a first test sample can be used to test for enzyme activities or the presence of metabolite molecules, and the second test sample can be used for PCR amplification to detect target nucleic acid. It is unexpected that a dried blood sample used for testing enzyme activities, which involves relatively long incubation periods, would subsequently yield a nucleic acid sample suitable for PCR. It is also unexpected that a DBS used for testing small metabolic molecules would subsequently yield a nucleic acid sample suitable for PCR because the hot (45 degrees Celsius) alcohol involved incubation used to extract acylcarnitines and amino acids (for example) is not expected to extract DNA to the degree sufficient for subsequent detection, even by sensitive methods such as PCR. Furthermore, in all cases these DBS are first saturated with the first or initial assay cocktail (either for enzyme activity or metabolite extraction); it is surprising that components of the assay cocktail did not interfere with nucleic acid release and release using two differing methods as provided herein (e.g., alkaline based or bead-based DNA isolation methods). Use of a single dried blood sample for two different assays beneficially expands the amount of information obtainable from the relatively small quantity of blood present in a dried blood sample.

Specific examples of processes for analyzing two or more differing targets from a single dried blood spot are described herein. In some aspects, processes as provided herein obtain first and second test samples from a single dried blood sample to assay one or more (e.g. optionally six or seven) enzymes relevant to lysosomal storage disorders, and also using the same DBS to further analyze by one or both of two different methods of nucleic acid purification to assay one or more genomic and/or non-genomic nucleic acid targets. Also provided are processes that obtain first and second samples from a single dried blood spot to assay one or more metabolic analytes (e.g. amino acids, acylcarnitines, lysophospholipids and nucleosides), and also using the same DBS for one or more different methods of nucleic acid isolation to assay one or more genomic and/or non-genomic nucleic acid targets.

As used herein, the term "dried blood sample" or "DBS" means a solid support holding dried blood from a subject. The solid support can be any absorbent material, for example, cotton, paper, polymer or a combination thereof. A common solid support is a filter paper "blood card." A dried blood spot is optionally a portion, or punch, of a filter paper blood card holding dried blood.

A subject as used herein is defined as any organism that expresses within the subject both protein and nucleic acid. A subject illustratively includes mammals, humans, non-human primates, horses, goats, cows, sheep, pigs, dogs, cats, rodents, insects, and cells.

As used herein, the term "quenching agent" means a chemical or combination of chemicals, that stops enzymatic activity of target proteins contained in or eluted from a dried blood sample.

As used herein, the term "quench solution" means the liquid sample that results after a quenching agent is added to a receptacle containing a dried blood sample together with an elution solution.

A dried blood sample useful in the processes provided contains or is suspected of containing one or more target compounds such as target enzyme(s), target nucleic acid(s), or target metabolic analyte(s). Target compounds can be contained in samples obtained from an individual, as well as from laboratory or synthetic materials, such as cell lines, and synthetic protein sources. Exemplary sample sources illustratively include: tissue homogenates; cell culture lysates; and biological fluids including urine, blood in liquid or dry form, tears, saliva, and cerebrospinal fluid. A sample can be further fractionated, if desired, to a fraction containing particular sample types. For example, a blood sample can be fractionated into serum or into fractions containing particular types of blood cells such as red blood cells or white blood cells (leukocytes). If desired, a sample can be a combination of samples from a subject such as a combination of a tissue and fluid sample, and the like. In some aspects, the sample is blood, which can be, for example, whole blood or a blood fraction thereof (e.g. plasma or serum) or reconstituted from a dried blood sample.

Methods for obtaining samples that preserve the activity or integrity of molecules in the sample are well known to those skilled in the art. Such methods include the use of appropriate buffers and/or inhibitors, including nuclease, protease and phosphatase inhibitors, which preserve or minimize changes in the molecules in the sample. The use of such preservatives is optionally. When used, however, such inhibitors include, for example, chelators such as ethylenediamine tetraacetic acid (EDTA), ethylene glycol bis(P-aminoethyl ether)N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al., Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W. B. Saunders, Philadelphia, (1999)). A sample also can be processed to eliminate or minimize the presence of one or more interfering substances.

For analysis, the dried blood is optionally eluted from a portion of the filter paper into an elution solution, which optionally contains a buffer such as phosphate buffered saline, HEPES, Tris, succinate, or other buffer, an alcohol, and optionally one or more protease or nuclease inhibitors. Specific examples of protease inhibitor conditions include for example, one or more of the following: AEBSF hydrochloride in a final concentration of 50 to 400 µg/ml, EDTA disodium dehydrate in a final concentration of 0.2 to 25 mg/ml, leupeptin hemisulfate in a final concentration of 0.5 to 1 µg/ml, and pepstatin A in a final concentration of 0.5 to 1 µg/ml. Protease inhibitor cocktails known commonly used in the art may be used. The use of a universal assay solution to extract a single dried blood sample, or other type of sample, for subsequent distribution into multiple assay reactions can be used for automatic and high throughput screening.

In some aspects a non-nucleotide target composition is or includes a protein or peptide. A peptide or protein as used herein are intended to mean a natural or synthetic compound containing two or more amino acids. Amino acids present in a peptide include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxy-cyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine. Accordingly, the term "peptide" or "protein" as used herein includes peptides having between 2 and about 1000 amino acids or having a molecular weight in the range of about 150-350,000 Daltons.

Specific illustrative examples of a peptide or protein include those related to one or more lysosomal storage disorders. Illustrative examples of proteins include but are not limited to β-Glucocerebrosidase, Sphingomyelinase, α-Glucosidase, Galactocerebrosidase, α-Galactosidase, α-Iduronidase, Iduronate 2-sulfatase, α-N-Acetylglucosaminidase, N-Acetylgalactosamine 6-sulfatase, Galactosidase, Arylsulfatase B, β-Glucuronidase, Tripeptidyl peptidase 1, or any combination thereof.

In some aspects a metabolite as used herein is a non-nucleotide target that is not a naturally occurring protein (or protein synthesized by a cell). Illustrative examples of a metabolite include an amino acid, acylcarnitine, lysophospholipid, and a nucleoside, among others. An amino acid may be a naturally occurring or non-naturally occurring amino acid, optionally as illustrated above. A nucleoside is understood in the art as a nitrogenous base covalently attached to a sugar (e.g. ribose or deoxyribose) an absent a phosphate group.

A nucleic acid is a target for isolation into a second test sample. Nucleic acids can include multiple nucleotides attached in the form of a single or double stranded polynucleotide that can be natural, or derived synthetically, enzymatically, or by cloning methods. Illustrative examples include cDNA, genomic DNA, mRNA, and RNA, oligonucleotides, oligonucleosides, and derivatives thereof. A nucleic acid is optionally a genomic nucleic acid or a non-genomic nucleic acid. A genomic nucleic acid is one that is formed of DNA as synthesized or as is present in the nucleus of a cell. A non-genomic nucleic acid is one that is found or the result of transcription of genomic DNA or is non-naturally produced and not structurally substantially equivalent to genomic nucleic acid. Illustrative examples of non-genomic nucleic acid include mRNA, tRNA, cDNA, processed DNA such as by cleavage and/or circularization, etc. Specific examples of genomic nucleic acid include the genes Survival Motor Neuron 1 (SMN1), Ribonuclease P/MRP Subunit P30 (RNAseP, or RRP30). Specific examples of non-genomic nucleic acid include T-cell receptor excision circles (TREC) and kappa-deleting element recombination circles (KREC).

Processes as provided herein include subjecting a dried blood sample to elution using a solution suitable for the elution of a non-nucleotide target. An elution solution optionally includes an alcohol. An alcohol is optionally used in an elution solution that is used for the isolation of a metabolite. An alcohol optionally includes a C1-3 linear or branched chain monoalcohol. In some aspects, an alcohol is methanol, ethanol, propanol, isopropanol, or derivatives thereof. Optionally, when detection of a metabolite is desired the alcohol including elution solution is incubated with the dried blood sample at an elevated temperature. An elevated temperature is optionally at or above 30 degrees Celsius, optionally 35 degrees Celsius, optionally 40 degrees Celsius, optionally 45 degrees Celsius, or optionally 50 degrees Celsius. This elevated temperature is sustained for an elution time. An elution time is optionally at or greater than 10 min, optionally 20 min, or optionally 30 minutes.

Optionally an elution solution includes one or more components suitable for sustaining enzymatic activity of one or more target proteins for a time sufficient to subject the proteins to further analyses such as by mass spectrometry, or enzymatic assay. Such materials optionally include a buffer and optionally a sugar, salt, or other desired molecule.

In some aspects a first target is an enzyme. An enzyme is optionally eluted into a solution that is suitable for sustaining enzymatic activity of one or more target proteins for a time sufficient to subject the proteins to further analyses. To this solution is optionally added one more substrates specific for the target protein of interest, and optionally one or more internal standards suitable for use in analyses my mass spectrometry and correspond, but are independently recognizable from a product of an enzymatic reaction with the one or more substrates. A reaction may be allowed to proceed for a time sufficient to produce a product in the presence of a suitable concentration of enzyme. Following the reaction time, a quenching agent is added to stop the enzymatic activity. Any suitable quenching agent may be used. Illustrative quenching agents include: 50/50 Ethyl acetate/methanol; 100% ethanol; 100% PBS-Tween; and 78% methanol; and 22% water plus 3 mM oxalic acid.

Following isolation of the non-nucleic acid target from the DBS, the solution containing the non-nucleic acid target, reaction product, or other material is then optionally subjected to further processing suitable for analyses by one or more detection methods such as ELISA, mass spectrometry, western blotting, among others.

The remaining DBS following separation of the elution solution is then itself used directly for the detection of one or more nucleic acids. The nucleic acids may be isolated such as by elution using one or more cell lysis agents, alkaline agents, or combinations thereof.

In some aspects a nucleic acid is isolated using a nucleic acid elution solution that includes one or more alkaline agents. Optionally, a pH of a nucleic acid elution solution is in the range of pH 11-12. An alkaline agent is optionally a hydroxide, optionally a hydroxide of Na, K, Ca, or other.

In other aspects, a nucleic acid is isolated using a cell lysis agent. A cell lysis agent is one suitable for lysing a cell that may be present in a DBS. Illustrative examples of cell lysis agents include a surfactant suitable to disrupt cell membranes. Illustrative examples of a surfactant include sodium dodecyl sulfate (SDS), Triton-X100, 3-[(3-cholamidopropyl)dimethylammonio]-1-propanesulfonate (CHAPS), among others.

In some aspects a nucleic acid is subjected to isolation by a bead based method such as bead based methods known in the art. Such bead based methods typically include a process for isolating nucleic acids whereby DNA, RNA or a nucleic acid binds to beads and a series of steps are taken to isolate, identify and/or analyze the bound nucleic acid. An illustrative bead based nucleic acid isolation method utilizes a CHEMAGIC 360 instrument and appropriate reagents for the detection of the target nucleic acid.

The first and second test samples can be used in a variety of assay formats such as enzymatic detection assays, mass spectrometry, PCR detection, RT-PCR detection, antibody assays (e.g. ELISA), among others. Aspects of an individual's health can be revealed by the presence, absence, amount, or activity of particular substances in the subject's blood. A variety of substances may be analyzed using DBS. Examples include small biomolecules such as amino acids and acylcarnitines; and large biomolecules such as proteins and nucleic acids (e.g. DNA and RNA). Well known medical tests include testing a panel of amino acids and acylcarnitines using mass spectrometry; testing of enzyme activities using fluorescent methods or mass spectrometry; and testing of DNA using PCR amplification of target DNA molecules.

In a real-time PCR assay as an exemplary detection method, a sample amplification is detected by accumulation of a fluorescent signal. The threshold cycle, or "$C_t$," is defined as the number of cycles required for the fluorescent signal to exceed the background noise. $C_t$ levels are inversely proportional to the amount of target nucleic acid in the sample—the lower the $C_t$, the more target nucleic acid; "mean $C_t$" is the average $C_t$ obtained after multiple (e.g. six (6)) replicates of the same DBS. "Delta $C_t$" is the difference in $C_t$s obtained when using the standard DNA extraction from a fresh punch and when using a punch that has went through the sequential elution protocol as indicated. Specifically, delta $C_t = C_t$ from punch that has went through sequential elution–$C_t$ from a fresh punch. Accordingly, when delta $C_t$ is a positive number, the $C_t$ for the sequential elution is higher. Higher $C_t$=lower sensitivity of the assay.

Various aspects are illustrated by the following non-limiting examples. The examples are for illustrative purposes and are not a limitation on any practice of the present processes. It will be understood that variations and modifications can be made without departing from the spirit and scope of the description. Reagents illustrated herein are commercially available or readily synthesized by well-known methods from readily commercially available precursors, and a person of ordinary skill in the art readily understands where such reagents may be obtained.

EXAMPLES

Example I

Six enzymatic lysosomal storage disorders are analyzed in a first test sample eluted from a DBS sample, followed by nucleic acid release using an alkaline method to assay four nucleic acid targets from the same DBS sample (second test sample) substantially as illustrated in FIG. 1. First, 10 an elution solution ("cocktail") was contacted with a DBS sample. The DBS sample was incubated with shaking 11 at 37 degrees Celsius with the elution solution for about 16-20 hours with shaking at 800 rpm. The elution solution contained enzyme-specific substrates (specific for enzymes related to a lysosomal storage disorder (LSD)) and corresponding deuterated internal standards dissolved in succinic acid buffer (85 mM, pH 4.7) containing 8 µM acarbose, 50 mM N-acetyl-D-galactosamine, 40 µM saccharic acid-1,4-lactone, 28 mM sodium taurocholate, and 0.6 mM zinc chloride. The enzymes tested, substrates and internal standards are for the lysosomal storage disorders as illustrated in Table 1.

TABLE 1

Exemplary Enzymes and Internal Standards for Various Disorders Assayed

| Disorder | Enzyme | ID | Role | Synonyms |
| --- | --- | --- | --- | --- |
| Gaucher | b-Glucocerebrosidase | ABG-S | Substrate | D-Glucosyl-b-1,1'-N-pentanoyl-D-erythro-sphingosine C5-Glucocerebroside |
| | | ABG-IS | Internal Standard | N-pentanoyl-D-erythro-sphingosine-d7 C5-Ceramide-d7 |
| N-P A/B | Sphingomyelinase | ASM-S | Substrate | N-hexanoyl-D-erythro-sphingosylphosphorylcholine C6-Sphingomyelin |
| | | ASM-IS | Internal Standard | N-hexanoyl-d7-D-erythro-sphingosine C6-d7-Ceramide |
| Pompe | a-Glucosidase | GAA-S | Substrate | (7-Benzoylamino-heptyl)-{2-[4-(3,4,5-trihydroxy-6-hydroxymethyl-tetrahydro-pyran-2-yloxy)-phenylcabamamoyl]-ethyl}-carbamic acid t-butyl ester |
| | | GAA-IS | Internal Standard | (7-d5-Benzoylamino-heptyl)-[2-[4-hydroxyphenylcabamamoyl]-ethyl]-carbamic acid t-butyl ester |
| Krabbe | Galactocerebrosidase | GALC-S | Substrate | D-Galactosyl-b1-1'-heptanoyl-D-erythro-sphingosine C7-Galactosylceramide |
| | | GALC-IS | Internal Standard | N-Heptanoyl-d-D-erythro-sphingosine C7-d5-ceramide |
| Fabry | a-Galactosidase | GLA-S | Substrate | (6-Benzoylamino-hexyl)-{2-[4-(3,4,5-trihydroxy-6-hydroxymethyl-tetrahydro-pyran-2-yloxy)-phenylcabamamoyl]-ethyl}-carbamic acid t-butyl ester |
| | | GLA-IS | Internal Standard | (7-d5-Benzoylamino-hexyl)-[2-[4-hydroxyphenyl cabamamoyl]-ethyl]-carbamic acid t-butyl ester |
| MPS-I | a-Iduronidase (Mucopolysaccharidosis Type 1) | IDUA-S | Substrate | 4-[[3-[Acetyl[6-(benzoylamino)hexyl]amino]-1-oxopropyl]amino]phenyl α-L-idopyranosiduronic acid |
| | | IDUA-IS | Internal Standard | (6-d5-Benzoylamino-hexyl)-[2-[4-hydroxyphenyl cabamamoyl]-ethyl]-carbamic acid acetyl ester |
| MPS-II | Iduronate 2-sulfatase | I2S-S | Substrate | α-L-Idopyranosiduronic acid, 4-[[3-[[6-(benzoylamino)hexyl](1-oxopentyl)amino]-1-oxopropyl]amino]phenyl, 2-(hydrogen sulfate sulfate) |
| | | I2S-IS | Internal Standard | 4-[[3-[Acetyl[[6-d5-(benzoylamino)hexyl]amino]-1-oxopropyl]amino]phenyl α-L-idopyranosiduronic acid |
| MPS-IIIB | a-N-Acetylglucosaminidase | NAGLU-S | Substrate | Butanamide, N-[3-[[4-[[2-(acetylamino)-2-deoxy-β-D-glucopyranosyl]oxy]phenyl]amino]-3-oxopropyl]-N-[6-[(1-oxopropyl)amino]hexyl]- |

TABLE 1-continued

Exemplary Enzymes and Internal Standards for Various Disorders Assayed

| Disorder | Enzyme | ID | Role | Synonyms |
|---|---|---|---|---|
| | | NAGLU-IS | Internal Standard | 4-[[1-oxo-3-[[6-[(1-oxopropyl-3-d3)amino]hexyl](1-oxopentyl)amino]propyl]amino]phenyl |
| MPS-IVA | N-Acetylgalactosamine 6-sulfatase | GALNS-S | Substrate | Benzamide, N-[6-[[3-[[4-[[2-(acetylamino)-2-deoxy-6-O-sulfo-β-D-galactopyranosyl]oxy]phenyl]amino]-3-oxopropyl](1-oxohexyl)amino]hexyl]-, sodium salt (1:1) |
| | | GALNS-IS | Internal Standard | 6-d5-Benzamide, N-[6-[[3-[[4-[[2-(acetylamino)-2-deoxy-β-D-galactopyranosyl]oxy]phenyl]amino]-3-oxopropyl](1-oxohexyl)amino]hexyl] |
| MPS-IVB | Galactosidase | GLB1-S | Substrate | Carbamic acid, N-[6-(propanoylamino)hexyl]-N-[3-[[4-(α-D-galactopyranosyloxy)phenyl]amino]-3-oxopropyl]-, 1,1-dimethylethyl ester |
| | | | Internal Standard | 4-[[1-oxo-3-[[6-[(1-oxopropyl-3-d3)amino]hexyl](1-oxopentyl)amino]propyl]amino]phenyl-, 1,1-dimethylethyl ester |
| MPS-VI | Arylsulfatase B | ARSB-S | Substrate | Benzamide, N-[5-[[3-[[4-[[2-(acetylamino)-2-deoxy-4-O-sulfo-β-D-galactopyranosyl]oxy]phenyl]amino]-3-oxopropyl](1-oxopentyl)amino]pentyl]-, sodium salt (1:1) |
| | | ARSB-IS | Internal Standard | 6-d5-Benzamide, N-[5-[[3-[[4-[[2-(acetylamino)-2-deoxy-β-D-galactopyranosyl]oxy]phenyl]amino]-3-oxopropyl](1-oxopentyl)amino]penyl]-, sodium salt (1:1) |
| MPS-VII | b-Glucuronidase | GUSB-S | Substrate | β-D-Galactopyranosiduronic acid, 4-[[1-oxo-3-[[6-[(1-oxobutyl)amino]hexyl](1-oxopentyl)amino]propyl]amino]phenyl |
| | | GUSB-IS | Internal Standard | 4-[[1-oxo-3-[[6-[(1-oxobutyl-3,4-d5)amino]hexyl](1-oxopentyl)amino]propyl]amino]phenyl |
| CLN2 | Tripeptidyl peptidase 1 | TPP1-S | Substrate | L-Alanyl-L-alanyl-L-phenylalanyl-N-[5-[[(1,1-dimethylethoxy)carbonyl]amino]pentyl]- |
| | | TPP1-IS | Internal Standard | Carbamic acid, N-[3-[[4-(aminomethyl)benzoyl]amino]hexyl]-, 1,1-di(methyl-d3)ethyl-2,2,2-d3 ester |

After incubation, 50/50 Ethyl acetate/methanol (100 µL) was used as a quenching agent and added to stop enzymatic activity 12. The resultant quench solution was transferred to a new receptacle 13 and subjected to further processing (14-17, FIG. 1). The quench solution was cleaned 13 using a liquid-liquid extraction approach that consisted of adding 400 µL ethyl acetate and 200 µL H₂O. The solution was separated by centrifugation for 5 minutes at 700×g 14, and the top layer was collected into a sampling plate 15. This material was evaporated at 40 degrees Celsius for 10-15 min 16 and reconstituted with a water/acetonitrile solution 17, thereby preparing a first test sample that is analyzed by mass spectrometry.

The DBS sample was then further processed to prepare a second test sample that included a nucleic acid 100-103 (FIG. 1). The DBS sample from quench step 12 above was contacted with 80 µL of a wash solution 100 (1×PBS with 0.1% Tween 20) and incubated for 5-10 minutes at 25 degrees Celsius 101. The wash solution was removed and nucleic acid elution solution (TRIS (30 mM) and KOH (20 mM)) was added and allowed to incubate with the DBS sample for 5-10 minutes at 25 degrees Celsius 102. The elution solution was then removed. Finally, a second aliquot of nucleic acid elution solution was applied to the DBS sample, and allowed to incubate for about 30 minutes at 70 degrees Celsius 103. The resultant solution is the second test sample.

The second test sample is subjected to PCR amplification that consisted of adding 3 µL of that sample into a well of a 384-well plate that contains 12 µL of an amplification cocktail. The amplification cocktail contains nuclease-free water, DNA polymerase, deoxyribonucleotides, magnesium chloride and other ions along with primers and probes that bind to four genomic and extra-genomic targets. The two genomic targets are the Survival Motor Neuron 1 (SMN1) and the Ribonuclease P/MRP Subunit P30 (RNAseP), while the two non-genomic targets are T-cell receptor excision circles (TREC) and kappa-deleting element recombination circles (KREC). The amplification takes place in a qPCR instrument. The primers and cycling conditions used are illustrated in Table 2. Results are illustrated in Table 3.

TABLE 2

Primer and probe sequences

| Target | Sequence | |
|---|---|---|
| TREC For | TTTGTAAAGGTGCCCACTCCT | SEQ ID NO: 1 |
| TREC Rev | TATTGCAACTCGTGAGAACGGTGAAT | SEQ ID NO: 2 |
| TREC Probe | CGGTGATGCATAGGCACCT | SEQ ID NO: 3 |
| KREC For | TCCCTTAGTGGCATTATTTGTATCACT | SEQ ID NO: 4 |
| KREC Rev | AGGAGCCAGCTCTTACCCTAGAGT | SEQ ID NO: 5 |
| KREC Probe | TCTGCACGGGCAGCAGGTTGG | SEQ ID NO: 6 |
| SMN For | CTTGTGAAACAAAATGCTTTTTAACATCCAT | SEQ ID NO: 7 |
| SMN Rev | GAATGTGAGCACCTTCCTTCTTTTT | SEQ ID NO: 8 |
| SMN1 Probe | AGG + GTT + T + C + A + GAC | SEQ ID NO: 9 |
| SMN2 Probe | AG + G + GTT + T + T + A + GAC | SEQ ID NO: 10 |
| RPP30 For | TTTGGACCTGCGAGCG | SEQ ID NO: 11 |
| RPP30 Rev | GAGCGGCTGTCTCCACAAGT | SEQ ID NO: 12 |
| RPP30 Probe | TTCTGACCTGAAGGCTCTGCGCG | SEQ ID NO: 13 |

Cycling Conditions

| Temperature | Duration (min) | Cycles |
|---|---|---|
| 37° C. | 2' | 1 |
| 94° C. | 5' | 1 |
| 93° C. | 10" | 40 |
| 60° C. | 30" | |
| 69° C. | 40" | |

TABLE 3

| Method | | Sample ID | KREC | RPP30 | SMN1 | TREC |
|---|---|---|---|---|---|---|
| Control | Non-Treated DBS | DBS Control 1 | | 21.9 | | |
| | | DBS Control 2 | 33.3 | 22.0 | 22.1 | 34.0 |
| | | DBS Control 3 | 29.7 | 21.9 | 22.2 | 29.0 |
| | | DBS Cord Blood | 29.6 | 21.9 | 26.1 | 32.9 |
| LSD ASSAY | Alkaline Example I | DBS Control 1 | | 26.2 | | |
| | | DBS Control 2 | 33.5 | 26.0 | 22.7 | 34.1 |
| | | DBS Control 3 | 29.3 | 25.5 | 22.5 | 29.2 |
| | | DBS Cord Blood | 30.6 | 30.7 | 28.4 | 32.6 |
| | Bead Based Extraction | DBS Control 1 | | 22.5 | | |
| | Example II | DBS Control 2 | 32.7 | 23.2 | 21.6 | 34.1 |
| | | DBS Control 3 | 28.8 | 22.9 | 21.6 | 28.8 |
| | | Cord | 31.3 | 27.7 | 25.4 | 32.5 |

A $C_t$ of less than 35 illustrates detectable DNA for the genomic targets of SMN1 and RPP30. A $C_t$ of less than 40 illustrated detectable DNA for the non-genomic targets of TREC and KREC. Variation in $C_t$ was typically less than +/−1.

Example II

Six enzymatic lysosomal storage disorders are analyzed in a first test sample eluted from a DBS, followed by nucleic acid release using a bead-based DNA isolation method to assay four nucleic acid targets from the same DBS sample (second test sample). The methods are described with reference to FIG. 2. First, 21 an elution solution ("cocktail") was contacted with a DBS sample and incubated with shaking 22 at 37 degrees Celsius with the elution solution for about 16-20 hours. The elution solution contained enzyme-specific substrates specific for enzymes implicated in lysosomal storage disorders and corresponding deuterated internal standards (Table 1) dissolved in succinic acid buffer (85 mM, pH 4.7) containing 8 μM acarbose, 50 mM N-acetyl-D-galactosamine, 40 μM saccharic acid-1,4-lactone, 28 mM sodium taurocholate, and 0.6 mM zinc chloride.

After incubation, 50/50 ethyl acetate/methanol was used as a quenching agent and added to stop enzymatic activity 23. The resultant quench solution was transferred to a new receptacle 24 and subjected to further processing (24-28, FIG. 2). The quench solution was cleaned 24 using a liquid-liquid extraction approach that consisted of adding 400 μL ethyl acetate and 200 μL $H_2O$. The solution was separated by centrifugation for 5 minutes at 700×g 25, and the top layer was collected into a sampling plate 26. This material was evaporated at 40 degrees Celsius for 10-15 minutes 27 and reconstituted with a water/acetonitrile solution 28, thereby preparing a first test sample for mass spectrometry analysis.

The DBS sample was further processed to prepare a second test sample for analyses of nucleic acid as illustrated at steps 200-203 (FIG. 2). 106 μl of a cell lysis solution (0.1 M Tris, 0.2 M NaCl, 5 mM EDTA, 1% (w/v) SDS, pH 8.1), 15 mM DTT and 50 μg proteinase K) was applied 200 to the DBS sample from quench step 23 above, and allowed to incubate with shaking for about 10 minutes at 25 degrees Celsius 201. The lysate was transferred into a 96 well plate and placed onto a Chemagic 360 instrument (PerkinElmer) 202. This sample was extracted using the PerkinElmer Chemagic 360 instrument 203 using a PerkinElmer 1030 DBS kit and ran quantitative PCR to detect the amplification of TREC, KREC, SMN1, RNAseP.

Table 3 shows data from Examples I and II. Polar quenching is sufficient to stop the enzyme activity at step 12 and 23 of FIGS. 1 and 2, respectively, yet still allow for adequate extraction and detection of DNA targets. These data indicate that a single DBS sample can be used to analyze both enzyme activity (e.g. activity of ABG, ASM, GAA, GALC, GLA, IDUA) and the presence and level of nucleic acid (e.g. T-cell receptor excision circles (TREC), kappa-deleting element recombination circles (KREC), Survival Motor Neuron 1 (SMN1), Ribonuclease P/MRP Subunit P30 (RNAseP)) from the same DBS.

Example III

Seven enzymatic lysosomal storage disorder targets (mucopolysaccharidoses (MPS)) from a first test sample eluted from a DBS sample, followed by nucleic acid release using an alkaline method to assay four nucleic acid targets from the same DBS sample (second test sample) were analyzed by the methods as illustrated in FIG. 1 and Example 1 substituting the enzymes specific for the indicated MPS disorders and corresponding internal standards presented in Table 1. Results are represented in Table 4.

TABLE 4

| Method | | Sample ID | KREC | RPP30 | SMN1 | TREC |
|---|---|---|---|---|---|---|
| Control Non-Treated DBS | | DBS Control 1 | | 21.9 | | |
| | | DBS Control 2 | 33.3 | 22.0 | 22.1 | 34.0 |
| | | DBS Control 3 | 29.7 | 21.9 | 22.2 | 29.0 |
| | | DBS Cord Blood | 29.6 | 21.9 | 26.1 | 32.9 |
| MPS ASSAY | Alkaline Example III | DBS Control 1 | | 25.5 | | |
| | | DBS Control 2 | 38.0 | 25.5 | 24.3 | 37.1 |
| | | DBS Control 3 | 32.6 | 25.9 | 24.6 | 32.5 |
| | | DBS Cord Blood | 32.7 | 28.8 | 27.0 | 34.6 |
| | Bead Based Extraction Example IV | DBS Control 1 | | 22.3 | | |
| | | DBS Control 2 | 32.2 | 22.5 | 21.0 | 33.4 |
| | | DBS Control 3 | 28.3 | 22.7 | 21.1 | 28.3 |
| | | Cord | 31.0 | 28.3 | 24.9 | 32.6 |

Example IV

Figure 2:
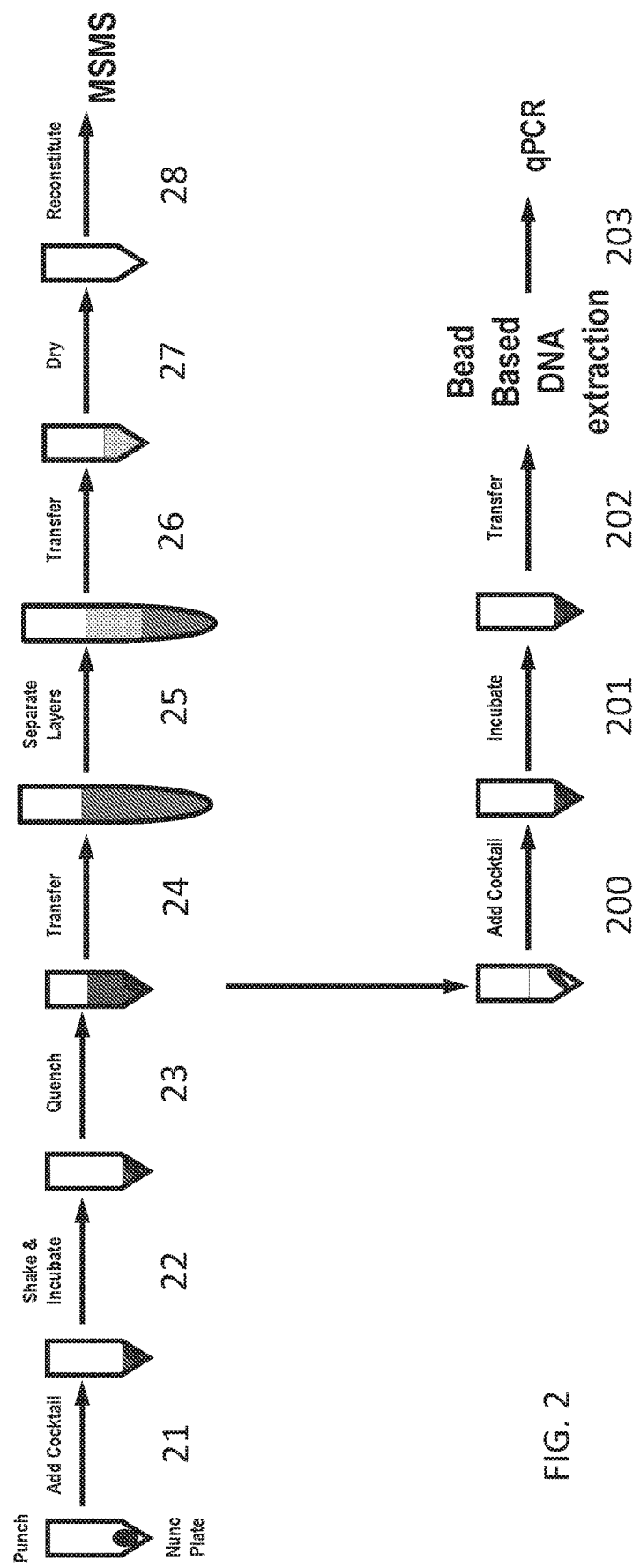
FIG. 2 illustrates an exemplary method of detecting the presence or absence of enzymes related to a series of lysosomal storage disorders and nucleic acids from both genomic and non-genomic sources using a bead based nucleotide extraction method from the same dried blood spot sample according to some aspects as provided herein.

Seven enzymatic lysosomal storage disorders (mucopolysaccharidoses (MPS)) from a first test sample eluted from a DBS sample, followed by nucleic acid release using a bead based extraction method to assay four nucleic acid targets from the same DBS sample (second test sample) were analyzed by the methods as illustrated in FIG. 2 and Example II substituting the enzymes specific for the indicated MPS disorders and corresponding internal standards presented in Table 1. Results are represented in Table 4.

Figure 3:
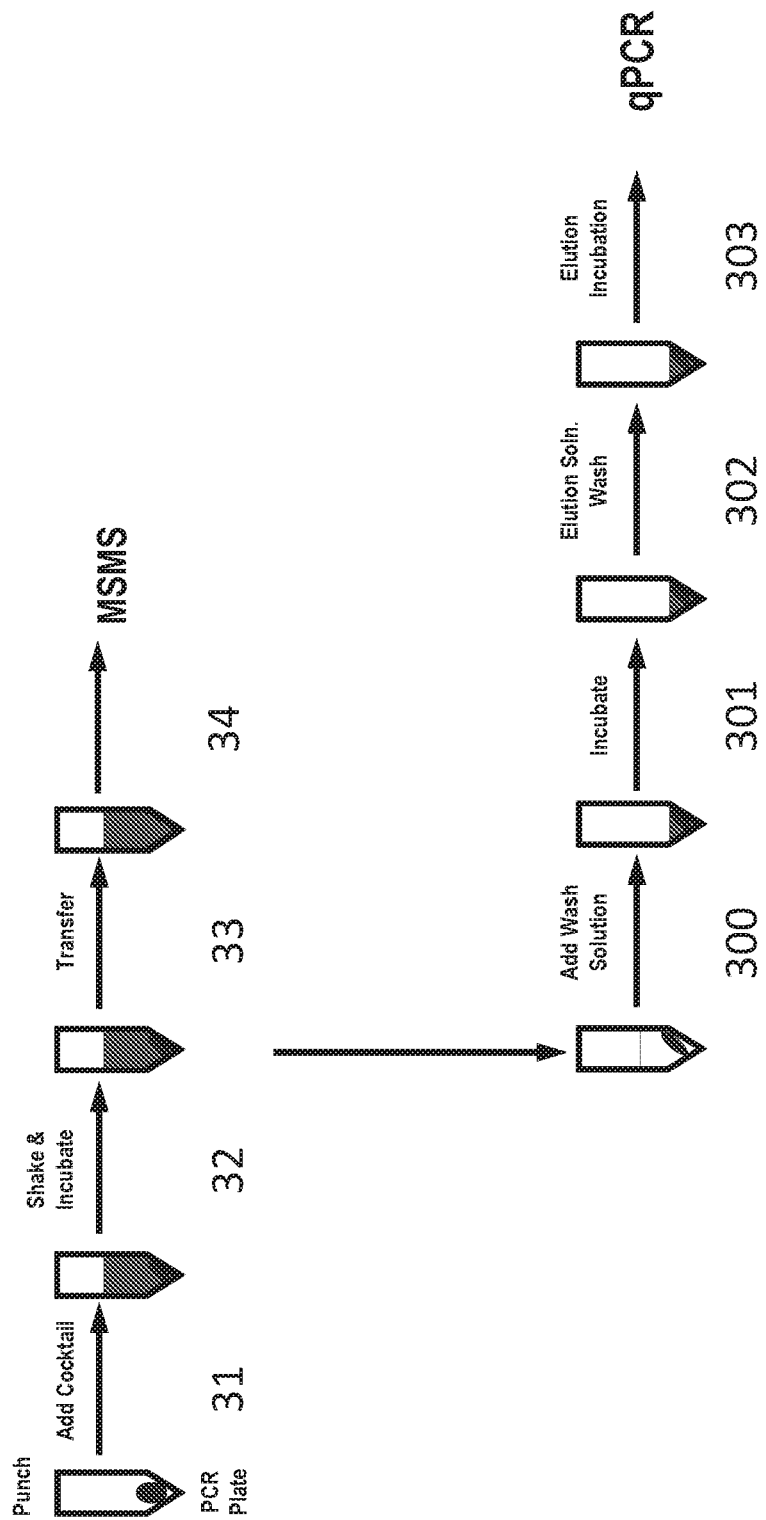
FIG. 3 illustrates an exemplary method of detecting the presence or absence of various blood metabolites and other targets from newborn blood and nucleic acids from both genomic and non-genomic sources using an alkaline based nucleotide extraction method from the same dried blood spot sample according to some aspects as provided herein.

Example V 56 metabolites in newborn blood are analyzed in a first test sample eluted from a DBS sample, followed by nucleic acid release using an alkaline method to assay four nucleic acid targets from the same DBS sample (second test sample) substantially as illustrated in FIG. 3. The analytes tested are illustrated in Table 5.

TABLE 5

| ANALYTE NAME | ABBREVIATION |
|---|---|
| Amino Acids | |
| Alanine | Ala |
| Arginine | Arg |
| Arginiosuccinic acid | Asa |
| Citruline | Cit |
| Glutamine\Lysine | Gln\Lys |
| Glutamic acid | Glu |
| Glycine | Gly |
| Leucine\Isoleucine\Hydroxyproline | Leu\Ile\Pro-OH |
| Methionine | Met |
| Orthithine | Orn |

TABLE 5-continued

| ANALYTE NAME | ABBREVIATION |
|---|---|
| Phenylalanine | Phe |
| Proline | Pro |
| Tyrosine | Tyr |
| Valine | Val |
| Carnitines | |
| Free Carnitines | C0 |
| Acetylcarnitine | C2 |
| Propionylcarnitine | C3 |
| Malonylcarnitine\3-Hydroxy-butrylcarnitine | C3DC\C4OH |
| Butrylcarnitine | C4 |
| Methylmalony\3-Hydroxy-isovalerylcarnitine | C4DC\C5OH |
| Isovalerylcarnitine | C5 |
| Tiglylcarnitine | C5:1 |
| Glutarylcarnitine\3-Hydroxy-hexanoylcarnitine | C5DC\C6OH |
| Hexanoylcarnitine | C6 |
| Adipylcarnitine | C6DC |
| Octanoylcarnitine | C8 |
| Octenoylcarnitine | C8:1 |
| Decanoylcarnitine | C10 |
| Decenoylcarnitine | C10:1 |
| Decadienoylcarnitine | C10:2 |
| Dodecanoylcarnitine | C12 |
| Dodecenoylcarnitine | C12:1 |
| Tetradecanoylcarnitine (Myristoylcarnitine) | C14 |
| Tetradecenoylcarnitine | C14:1 |
| Tertadecadienoylcarnitine | C14:2 |
| 3-Hydroxy-tetradecanoylcarnitine | C14OH |
| Hexadecanoylcarnitine (Palmitoylcarnitine) | C16 |
| Hexadecenoylcarnitine | C16:1 |
| 3-Hydroxy-hexadecanoylcarnitine | C16OH |
| 3-Hydroxy-hexadecenoylcarnitine\ Heptadecanoylcarnitine | C16:OH\C17 |
| Octadecanoylcarnitine (Stearoylcarnitine) | C18 |
| Octadecenoylcarnitine (Oleylcarnitine) | C18:1 |
| Octadecadienoylcarnitine (Linoleycarnitine) | C18:2 |
| 3-Hydroxy-octadecanoylcarnitine | C18OH |
| 3-Hydroxy-octadecenoylcarnitine | C18:1OH |
| 3-Hydroxy-octadecadienoylcarnitine | C18:2OH |
| Eicosanoylcarnitine (Arachidoylcarnitine) | C20 |
| Docosanoylcarnitine (Behenoylcarnitine) | C22 |
| Tetracosanoylcarniting (Lignoceroylcarniting) | C24 |
| Hexacosanoylcarnitine (Cerotoylcarnitine) | C26 |
| Ketones | |
| Succinylacetone | SA |
| Nucleosides | |
| Adenosine | ADP |
| 2'deoxyadenosine | D-ADO |
| Lysophospholipids | |
| C20:0 lysophophatidycholine | C20:0-LPC |
| C20:0 lysophophatidycholine | C20:0-LPC |
| C22:0 lysophophatidycholine | C22:0-LPC |
| C26:0 lysophophatidycholine | C26:0-LPC |

An elution solution ("cocktail") (125 µL) was contacted with a DBS sample 31. The elution solution contained various internal standards dissolved in 78% MeOH/22% $H_2O$ with 3 mM oxalic acid. The DBS sample was incubated with shaking at about 45 degrees Celsius at 700 rpm with the elution solution for about 30 minutes 32. The elution solution was separated from the DBS sample to produce the first test sample, which was then transferred to a sample plate 33. This sample was analyzed by mass spectrometry using a PerkinElmer Neobase2 kit for detecting amino acids, acylcarnitines, lysophospholipids and nucleosides 34.

The DBS sample remaining after separation from the elution solution at 32 was processed to produce a second test sample for nucleic acid analyses using an alkaline method. First, the DBS sample was contacted with 80 µl of a wash solution (1×PBS with 0.1% Tween 20) 300, and the DBS sample incubated with shaking for 5-10 minutes at 25 degrees Celsius 301. The wash solution was removed and nucleic acid releasing solution (TRIS (30 mM) and KOH (20 mM)) was added and allowed to incubate with the DBS sample for 5-10 minutes at 25 degrees Celsius 302 with shaking. The wash solution was then removed. Finally, a second aliquot of nucleic acid releasing solution was applied to the DBS sample and allowed to incubate for about 30 minutes at 70 degrees Celsius 303. The resultant solution is the second test sample that was subjected to quantitative PCR to detect the amplification of TREC, KREC, SMN1, RNAseP. Data is presented in Table 6.

TABLE 6

| | Method | Sample ID | KREC | RPP30 | SMN1 | TREC |
|---|---|---|---|---|---|---|
| Control | Non-Treated DBS | DBS Control 1 | | 21.9 | | |
| | | DBS Control 3 | 29.7 | 21.9 | 22.2 | 29.0 |
| Metabolite Assay | Alkaline Example V | DBS Control 1 | 38.0 | 24.2 | 34.7 | |
| | | DBS Control 3 | 30.9 | 22.0 | 22.2 | 30.1 |
| | Bead Based Assay Example VI | DBS Control 1 | | 24.6 | 35.9 | |
| | | DBS Control 3 | 31.3 | 22.3 | 22.6 | 30.3 |

Figure 4:
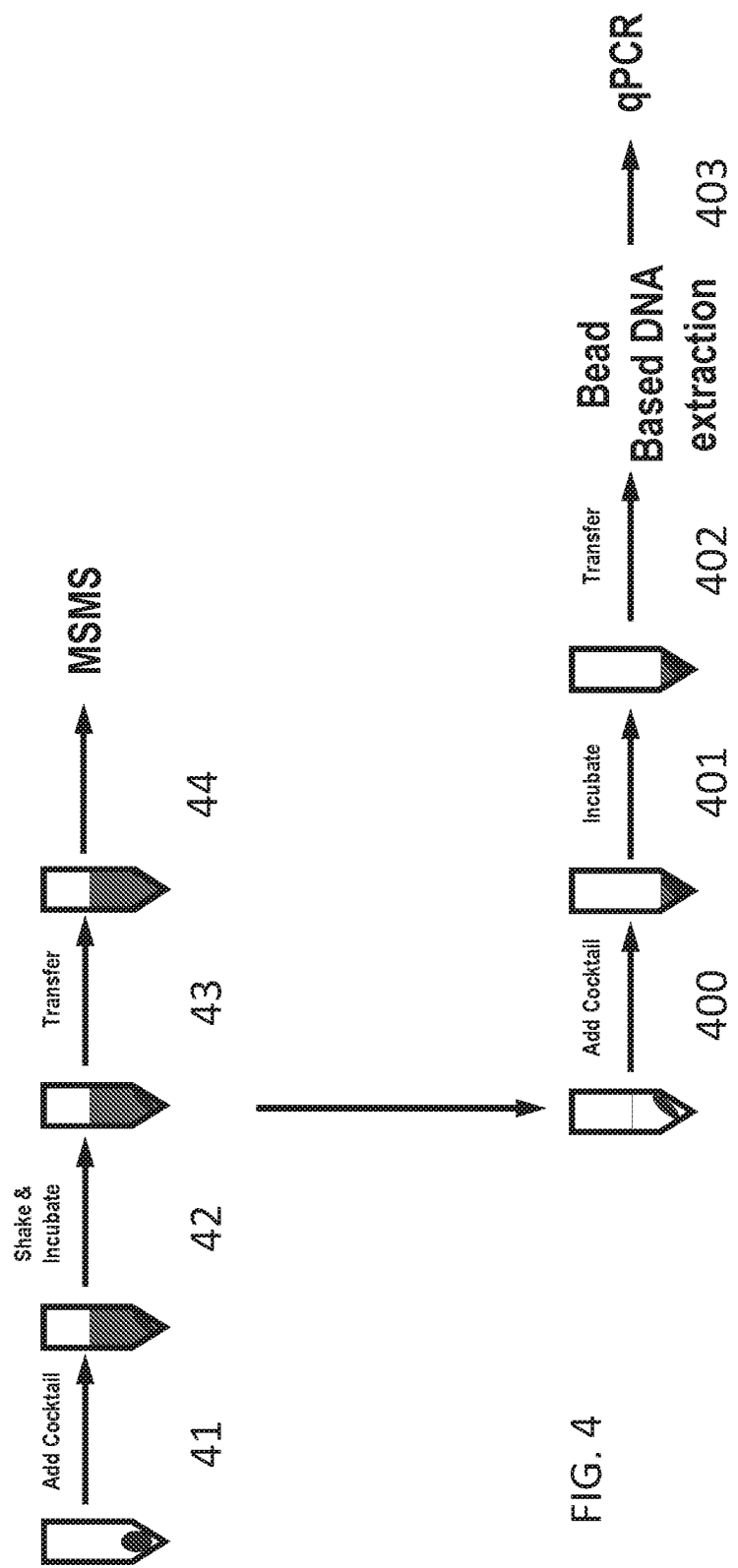
FIG. 4 illustrates an exemplary method of detecting the presence or absence of various blood metabolites and other targets from newborn blood and nucleic acids from both genomic and non-genomic sources using a bead based nucleotide extraction method from the same dried blood spot sample according to some aspects as provided herein.

Example VI 56 metabolites in newborn blood are analyzed in a first test sample eluted from a DBS sample, followed by nucleic acid release using an bead based method to assay four nucleic acid targets from the same DBS sample (second test sample) substantially as illustrated in FIG. 4.

First, 41 and an elution solution ("cocktail") was contacted with a DBS sample. The elution solution contained various internal standards as in Example V dissolved in 78% MeOH/22% $H_2O$ with 3 mM oxalic acid. The DBS sample was incubated with shaking at about 45 degrees Celsius with the elution solution for about 30 minutes with shaking at 700 rpm 42. The elution solution was separated from the DBS sample to produce the first test sample that was then transferred to a sample plate 43. This sample was analyzed by mass spectrometry using a PerkinElmer Neobase2 kit for detecting amino acids, acylcarnitines, lysophospholipids and nucleosides 44. The DBS sample remaining after separation from the elution solution was processed to produce a second test sample for nucleic acid analyses using a bead-based extraction method substantially as illustrated in FIG. 4. A cell lysis solution (0.1 M Tris, 0.2 M NaCl, 5 mM EDTA, 1% (w/v) SDS, pH 8.1), 15 mM DTT and 50 µg proteinase K) was applied to the DBS sample 400, and allowed to incubate with shaking for about 10 minutes at 25 degrees Celsius with shaking at 1000 rpm 401. The nucleic acid releasing solution was then collected to produce the second test sample that was loaded into a Chemagic360 instrument 402. This sample was extracted with the PerkinElmer Chemagic360 instrument 403 using a PerkinElmer 1030 DBS kit and analyzed by quantitative PCR to detect amplification of TREC, KREC, SMN1, RNAseP. Table 5 illustrates the results of the assays of Examples V and VI demonstrating for both methods using an elution solution (cocktail) plus heat is sufficient to detect acylcarnitine and amino acid deficiencies yet still allow for adequate extraction and detection of DNA targets. Therefore, a single DBS can be used to measure both 56 analytes and both genomic and non-genomic nucleic acid targets.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular aspects of the invention, but is not meant to be a limitation upon the practice thereof. The following claims, including all equivalents thereof, are intended to define the scope of the invention.

We claim:

1. A method for analyzing the presence or absence of both enzyme and nucleic acid targets present in a single dried blood sample, comprising:
   obtaining a dried blood sample;
   contacting the dried blood sample with an elution solution comprising a C1-3 linear or branched chain monoalcohol;
   incubating the dried blood sample in the elution solution for a time sufficient to elute one or more non-nucleotide targets;
   separating the dried blood sample and the elution solution, thereby preparing a first test sample comprising the non-nucleotide targets and a separated dried blood sample;
   contacting the separated dried blood sample with a nucleic acid releasing solution suitable for eluting nucleic acids; and
   incubating the separated dried blood sample in the nucleic acid releasing solution for a time sufficient to elute the nucleic acids, thereby preparing a second test sample.

2. A method for analyzing the presence or absence of both enzyme and nucleic acid targets present in a single dried blood sample, comprising:
   obtaining a dried blood sample;
   contacting the dried blood sample with an elution solution capable of sustaining enzymatic activity of one or more target proteins;
   incubating the dried blood sample in the elution solution for a time sufficient to elute the one or more target proteins;
   subsequently contacting the post-incubation dried blood sample with a quenching agent to produce a quench solution that inhibits enzymatic activity of the one or more target proteins;
   separating the dried blood sample and the quench solution, thereby preparing a first test sample comprising the one or more target proteins and a separated dried blood sample;
   contacting the separated dried blood sample with a nucleic acid releasing solution suitable for eluting nucleic acids; and
   incubating the separated dried blood sample in the nucleic acid releasing solution for a time sufficient to elute the nucleic acids, thereby preparing a second test sample.

3. The method of claim 1, wherein separating the dried blood sample from the elution solution is achieved by removing the elution solution.

4. The method of claim 1, wherein separating the dried blood sample from nucleic acid releasing solution is achieved by removing the nucleic acid releasing solution.

5. The method of claim 1, further comprising washing the separated dried blood sample prior to contacting the dried blood sample with nucleic acid releasing solution.

6. The method of claim 1, wherein the elution solution further comprises water.

7. The method of claim 1 wherein the elution solution further comprises an acid, optionally oxalic acid.

8. The method of claim 1 wherein the C1-3 linear or branched chain monoalcohol comprises methanol.

9. The method of claim 1 wherein the nucleic acid releasing solution comprises an alkaline agent.

10. The method of claim 9 wherein the alkaline agent is a hydroxide of K, Na, or Ca.

11. The method of claim 1 wherein the nucleic acid releasing solution comprises an agent capable of lysing a cell wall.

12. The method of claim 11 wherein the agent is a surfactant.

13. The method of claim 12 wherein the surfactant is sodium dodecyl sulfate.

14. The method of claim 1 further comprising contacting the nucleic acid releasing solution with one or more beads capable of bonding to a nucleic acid.

15. The method of claim 1 wherein the first test sample is subjected to analysis by mass spectrometry.

16. The method of claim 1 wherein the second test sample is subjected to analysis by a quantitative polymerase chain reaction.

17. A method for sequentially testing the presence or level of one or more metabolic analytes and the presence or level of nucleic acid targets using a single dried blood sample, the method comprising
   subjecting the first test sample prepared according to claim 1 to analysis by mass spectrometry; and
   subjecting the second test sample prepared according to claim 1 to analysis by polymerase chain reaction.

18. The method of claim 17 wherein the mass spectrometry is tandem mass spectrometry.

19. The method of claim 17 wherein the polymerase chain reaction is quantitative PCR.

20. The method of claim 2, further comprising washing the separated dried blood sample prior to contacting the dried blood sample with nucleic acid releasing solution.

* * * * *